United States Patent
Guyuron et al.

(10) Patent No.: US 6,471,985 B2
(45) Date of Patent: *Oct. 29, 2002

(54) USE OF RTV SILICONE COMPOSITIONS FOR WOUND DRESSING

(76) Inventors: Bahman Guyuron, 29017 Cedar Rd., Lyndhurst, OH (US) 44124; Michael Doliveck, Suite 206, 117 Pacific St., Santa Monica, CA (US) 90405

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/325,981

(22) Filed: Jun. 4, 1999

(65) Prior Publication Data

US 2002/0010299 A1 Jan. 24, 2002

(51) Int. Cl.⁷ .......................... A61L 15/22; A61K 9/70; C08G 77/08; C08G 77/06
(52) U.S. Cl. .................. 424/445; 424/443; 528/15; 528/31; 528/32; 528/33; 528/34; 528/37; 528/901; 524/860; 524/861; 524/862; 524/863; 525/478; 427/2.31; 427/155; 604/304; 602/52; 602/904; 128/DIG. 21
(58) Field of Search .................. 424/443, 445; 602/52, 904; 604/304; 128/DIG. 21; 427/2.31, 155; 528/15, 31, 32, 33, 34, 37, 901; 525/478; 524/860, 861, 862, 863

(56) References Cited

U.S. PATENT DOCUMENTS

| | | | | |
|---|---|---|---|---|
| 4,638,800 A | * | 1/1987 | Michel | 128/303.1 |
| 4,791,149 A | * | 12/1988 | Pocknell | 523/111 |
| 4,987,893 A | * | 1/1991 | Salamone et al. | 128/156 |
| 5,010,115 A | * | 4/1991 | Grisoni | 521/154 |
| 5,103,812 A | * | 4/1992 | Salamone et al. | 602/52 |
| 5,153,231 A | * | 10/1992 | Bouquet et al. | 521/88 |

* cited by examiner

Primary Examiner—Robert Dawson
Assistant Examiner—Jeffrey B. Robertson
(74) Attorney, Agent, or Firm—Renner, Otto, Boisselle & Sklar, LLP

(57) ABSTRACT

In one embodiment, the present invention relates to a method of treating a wound, involving applying to the wound a room temperature vulcanizing silicone composition comprising a crosslinkable polymer, a crosslinking agent, and a catalyst; permitting the room temperature vulcanizing silicon composition to cure thereby forming a membrane having a thickness from about 0.1 mm to about 5 mm; and removing the membrane from the wound after at least about 1 day.

37 Claims, No Drawings

USE OF RTV SILICONE COMPOSITIONS FOR WOUND DRESSING

TECHNICAL FIELD

The present invention relates to treating skin wounds, especially those resulting from surgery, by applying a specifically defined silicone composition over the wounds.

BACKGROUND OF THE INVENTION

Skin wounds, whether caused by injury or surgery, raise several concerns. One concern is scarring. Scarring in many instances results in a diminished sense of touch, weak regions in the skin (where scars join unwounded skin), and obvious cosmetic problems. Scarring is presently associated with injury and surgical wounds. It is therefore desirable to minimize scarring.

Another concern is infection or contamination. This is because an exposed wound is an ideal breeding ground for harmful bacteria. Even with conventional dressings, infections are fairly common. It is therefore desirable to minimize infections.

Yet another concern is providing an effective wound dressing. Wound dressings must adhere to a wound, yet possess releaseability characteristics enabling a non-damaging removal from the wound. Wound dressings must also stretch/flex to accommodate skin or bodily movement. Depending upon where the dressing is located, it is sometimes desirable to decrease the conspicuousness, for example facial dressings. Wound dressings are characterized by frequent changing which is not only time consuming, but also leads to the undesirable production of medical waste. It is therefore desirable to provide improved wound dressings.

Laser surgery is associated with using a small, powerful beam of light to make a small burn or opening. Typically, the laser is used to remove unwanted, damaged, or diseased cells (layers of skin) without harming the surrounding healthy cells. Laser surgery is frequently used to treat sun-damaged skin, wrinkles, and scars including acne scars, among other uses. An undesirable consequence of laser surgery is post-operative redness.

Laser surgery healing involves skin regeneration, similar to healing conventional burn wounds. This is different from traditional surgery using a scalpel. Traditional surgery healing involves skin repair. Thus, there are unique demands associated with treating a laser surgery wound compared with traditional surgery wounds. Since laser surgery is a developing medical procedure, improvements in treating laser surgery wounds are necessary.

SUMMARY OF THE INVENTION

The present invention relates to treating skin wounds, especially those resulting from laser surgery, by applying a specifically defined silicone composition over the wounds. The present invention provides improved wound dressings in that the silicone based dressings do not need to be changed every day, as conventional dressings require. The silicone based dressings adequately adhere to a wound, yet possess releaseability enabling the non-damaging removal of the dressing from the wound. The silicone based dressings further minimize scarring and minimize potential infections. Another benefit associated with the silicone based dressings used in accordance with the present invention is the reduction of post-operative redness (reduction of the hue intensity of the redness as well as the duration of any redness).

In one embodiment, the present invention relates to a method of treating a wound, involving applying to the wound a room temperature vulcanizing silicone composition comprising a crosslinkable polysiloxane, a crosslinking agent, and a catalyst; permitting the room temperature vulcanizing silicone composition to cure thereby forming a membrane having a thickness from about 0.1 mm to about 5 mm; and removing the membrane from the wound after at least about 1 day.

In another embodiment, the present invention relates to a method of treating a laser surgery wound, involving combining a first composition comprising a first crosslinkable polysiloxane and a crosslinking agent with a second composition comprising a second crosslinkable polysiloxane and a platinum catalyst to form a room temperature vulcanizing silicone composition comprising the first and second crosslinkable polysiloxanes, the crosslinking agent, and the platinum catalyst; applying to the laser surgery wound the room temperature vulcanizing silicone composition; permitting the room temperature vulcanizing silicone composition to cure thereby forming a substantially transparent membrane having a thickness from about 0.25 mm to about 3 mm; and removing the substantially transparent membrane from the laser surgery wound after at least about 2 days.

In yet another embodiment, the present invention relates to a method of treating a laser surgery wound, involving combining a first composition comprising a first crosslinkable polysiloxane and a crosslinking agent with a second composition comprising a second crosslinkable polysiloxane and a platinum catalyst to form a room temperature vulcanizing silicone composition comprising the first and second crosslinkable polysiloxanes, the crosslinking agent, and the platinum catalyst; applying to the laser surgery wound the room temperature vulcanizing silicone composition; permitting the room temperature vulcanizing silicone composition to cure thereby forming a substantially transparent membrane having a thickness from about 0.25 mm to about 3 mm; and removing the substantially transparent membrane from the laser surgery wound after at least about 4 days.

DESCRIPTION OF THE PREFERRED EMBODIMENTS

The present invention generally provides treatments for surgical wounds. In one embodiment, the present invention provides a method of facilitating healing of surgical wounds. In another embodiment, the present invention provides a method of preventing infection of surgical wounds. In yet another embodiment, the present invention provides a method of minimizing scarring due to surgical procedures. In a specific embodiment, the present invention provides a method of facilitating healing of surgical wounds caused by laser surgery.

The present invention involves using a room temperature vulcanizing (RTV) silicone composition to cover surgical wounds, especially wounds from laser surgery, to facilitate at least one of wound healing, infection prevention, and scarring minimization. The RTV silicone composition is preferably an addition cured RTV silicone composition, although a condensation cured RTV silicone composition may be employed. In one embodiment, the RTV silicone composition is a two-part RTV silicone composition. In another embodiment, the RTV silicone composition is an RTV silicone elastomer.

The RTV silicone composition contains at least three components; namely; a crosslinkable polysiloxane, a crosslinking agent, and a catalyst. In many embodiments, the RTV silicone composition further contains at least one optional additives including fillers and medicaments. In embodiments where the RTV silicone composition is a two-part RTV silicone composition, one part contains the crosslinking agent while a second part contains the catalyst. Typically both parts contain the crosslinkable polysiloxane, and one or both parts may contain at least one optional additive.

The RTV silicone composition contains a crosslinkable polysiloxane. Crosslinkable polysiloxanes are known as curable silicone prepolymers; that is, a polysiloxane having one or more functional groups, such as vinyl groups, which enable the prepolymer to be polymerized or cured to a state of higher molecular weight. Suitable silicone prepolymers are known in the art and are described, for example, in "Silicones", *Kirk-Othmer Encyclopedia of Chemical Technology,* 3rd Ed., 20, 922–962 (1982), which is incorporated by reference in this regard.

Crosslinkable polysiloxanes are made by an equilibrium process from siloxanes or other polysiloxanes and typically range in viscosity from about 0.01 Pa s to 2500 Pa s. The preferred molecular weight of the crosslinkable polysiloxane often depends upon the desired viscosity of the RTV silicone composition prior to crosslinking. In general, as the molecular weight is increased, the viscosity of the uncrosslinked composition correspondingly increases.

In one embodiment, a crosslinkable polysiloxane is represented by Formula I:

Formula I

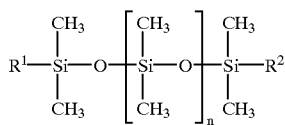

wherein $R^1$ and $R^2$ are independently organofunctional groups and n is from about 10 to about 6,000.

The groups $R^1$ and $R^2$ of Formula I represent the "terminal" portions of the polymer chain and are often the sites for the attachment of one or more functional groups, i.e., the groups which participate in the crosslinking reaction. In one embodiment, one or more sites depicted in Formula I as having methyl groups instead contain the one or more organofunctional groups. Likewise, $R^1$ and/or $R^2$ may not be the site of the one or more organofunctional groups. Therefore, Formula I is intended to merely represent a "typical" crosslinkable polysiloxane with terminal functional groups. The site of attachment of the functional groups is not presently believed to be particularly important. In one embodiment, the average value of n is from about 25 to about 5,000. In another embodiment, the average value of n is from about 50 to about 2,500. In yet another embodiment, the average value of n is from about 100 to about 1,000. Mixtures of more than one molecular weight may likewise be utilized.

The one or more organofunctional groups preferably possess an unsaturated carbon carbon bond, such as an unsaturated aliphatic group. In one embodiment, each organofunctional group independently is a hydrocarbyl group containing from 1 to about 20 carbon atoms, and preferably from about 2 to about 10 carbon atoms. Examples of organofunctional groups include alkenyl, cycloalkenyl, such as vinyl, allyl, 1-hexenyl and cyclohexenyl. A preferred organofunctional group is a vinyl group.

When certain properties are desired, other monovalent hydrocarbyl and halogenated monovalent hydrocarbyl groups (e.g., alkyls, phenyl, cyanoethyl, and trifluoropropyl) can be substituted for the methyl groups of Formula I.

The term "hydrocarbyl" as used herein includes hydrocarbon as well as substantially hydrocarbon groups. Substantially hydrocarbon describes groups which contain heteroatom substituents which do not alter the predominantly hydrocarbon nature of the group. Examples of hydrocarbyl groups include hydrocarbon substituents, i.e., aliphatic (e.g., alkyl or alkenyl) and substituted aliphatic substituents, alicyclic (e.g., cycloalkyl, cycloalkenyl) substituents, aromatic-, aliphatic- and alicyclic-substituted aromatic substituents. Heteroatoms include, by way of example, halogens including fluorine and chlorine, nitrogen, oxygen and sulfur. In one embodiment, the crosslinkable polysiloxane is a diorgano polysiloxane.

Accordingly, in another embodiment, the crosslinkable polysiloxane is represented by Formula II:

Formula II

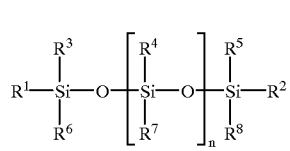

wherein $R^1$ and $R^2$ are independently hydrogen, hydroxyl, and organofunctional groups, $R^3$, $R^4$, $R^5$, $R^6$, $R^7$, and $R^8$ are independently hydrogen, and hydrocarbyl groups containing from 1 to about 20 carbon atoms and n is from about 10 to about 6,000. For example, $R^1$, $R^2$, $R^3$, $R^4$, $R^5$, $R^6$, $R^7$, and $R^8$ are radicals independently selected from hydrogen, hydroxyl, aryl and halogenated aryl such as phenol, methylphenol, chlorophenol, naphthyl, alkyl such as methyl ethyl, etc.; aliphatic and cycloaliphatic such as methyl, ethyl, propyl, cyclohexyl, cyclobutyl, etc., alkenyl such as vinyl, allyl, etc.; and cyanoalkyl such as cyanoethyl, cyanopropyl, cyanobutyl.

Examples of the crosslinkable polysiloxane include dimethyl polysiloxane, dimethyl diphenyl polysiloxane, and trifluoropropyl methyl polysiloxane blocked with an appropriate end group, such as a vinyl group.

The preferred amount of the crosslinkable polysiloxane component varies depending upon the desired physical properties of the RTV silicone composition (such as the desired uncured viscosity, cured hardness, etc.). In part due to the wide range of acceptable molecular weights for the crosslinkable polysiloxane component and the many types of adjuvants which may be added to the RTV silicone composition this amount varies widely. In one embodiment, the amount of the crosslinkable polysiloxane in the RTV silicone composition is from about 10% to about 99% by weight. In another embodiment, the amount of the crosslinkable polysiloxane in the RTV silicone composition is from about 20% to about 90% by weight. In yet another embodiment, the amount of the crosslinkable polysiloxane in the RTV silicone composition is from about 25% to about 80% by weight.

The crosslinking agent contains at least one silicon-hydrogen linkage and can be a polymeric compound or a compound that is not polymeric. These compounds are known in the art and are disclosed, for example, in U.S. Pat. Nos. 3,159,662; 3,220,972; and 3,410,886; which are hereby incorporated by reference in this regard. The crosslinker containing the silicon-hydrogen linkage preferably contains at least about two silicon-hydrogen linkages per molecule, with preferably no more than about three hydrogen atoms attached to any one silicon atom. For example, in one embodiment, the crosslinking agent is an organohydrogenpolysiloxane.

In one embodiment, compounds having a silicon-bonded hydrogen atom which can be used as the crosslinking agent in the present invention are organohydrogensilanes having empirical Formula III:

$$(H)_a(R^9)_b Si_c \qquad \text{Formula III}$$

wherein each $R^9$ can be the same or different and represents an organic group, preferably selected from the group consisting of monovalent hydrocarbyl groups, monovalent hydroalkoxyl groups and halogenated monovalent hydrocarbyl groups, any of which containing from 1 to about 20 carbon atoms, c is from 1 to about 10,000, a is at least about 2 and less than or equal to c when c is greater than 1, and the sum of a and b equals the sum of 2 and two times c.

In another embodiment, compounds having a silicon-bonded hydrogen atom which can be used as the crosslinking agent in the present invention are organohydrogencyclopolysiloxanes having empirical Formula IV:

$$H_d R^9_e (SiO)_f \qquad \text{Formula IV}$$

wherein $R^9$ is as defined above, f is from about 3 to about 18, d is at least about 2 and less than or equal to f, and the sum of d and e equals two times f.

In another embodiment, compounds having a silicon-bonded hydrogen atom which can be used as the crosslinking agent in the present invention are organohydrogenpolysiloxane polymers or copolymers having empirical Formula V:

$$(H)_g(R^9)_h Si_j O_{(j-1)} \qquad \text{Formula V}$$

wherein $R^9$ is as defined above, j is from about 2 to about 10,000, g is at least about 2 and less than or equal to j, and the sum of g and h equals the sum of about 2 and two times j.

Specific groups represented by $R^9$ include, for example, alkyl groups having from 1 to about 18 carbon atoms, such as methyl, ethyl, propyl, octyl, and octadecyl groups, cycloalkyl groups having from about 5 to about 7 ring carbon atoms, such as cyclohexyl and cycloheptyl groups, aryl groups having from about 6 to about 18 carbon atoms, such as phenyl, naphthyl, tolyl, xylyl groups, alkoxyl groups having from 0 to about 18 carbon atoms, such as hydroxyl, methoxyl, ethoxyl, propoxyl, and combinations of alkyl and aryl groups, such as aralkyl groups, such as, benzyl and phenylethyl, and halo-substituted groups thereof, such as chloromethyl, chlorophenyl, and dibromophenyl groups. In one embodiment, the $R^9$ group is methyl or both methyl and phenyl. In another embodiment, the $R^9$ group is an unsaturated aliphatic group having from 1 to about 20 carbon atoms, such as alkenyl and cycloalkenyl groups, including vinyl, allyl and cyclohexenyl groups. When the $R^9$ group is a group with aliphatic unsaturation, the silicon compound containing silicon-hydrogen linkages can be reacted with itself to form a polymer.

In one embodiment, the compound having silicon-bonded hydrogen useful as the crosslinking agent in the present invention is a polyorganohydrogenpolysiloxane having general Formula VI

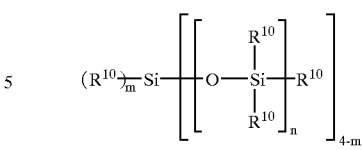

Formula VI wherein each $R^{10}$ is independently hydrogen or hydrocarbyl containing from 1 to about 20 carbon atoms. In another embodiment, each $R^{10}$ is independently hydrogen, an alkyl group containing from 1 to about 18 carbon atoms, a cycloalkyl group containing from about 3 to about 12 carbon atoms, or a phenyl group (substituted or unsubstituted), at least about two but not more than about one-half of all the $R^{10}$ groups in the siloxane are hydrogen, m is 0,1,2, or 3, and n has an average value from 1 to about 10,000.

The amount of the crosslinking agent component varies to provide the desired degree of crosslinking of the RTV silicone composition. In part, due to the wide range of acceptable molecular weights for the crosslinkable polysiloxane, this amount can be adequately described in terms of the ratio of Si—H groups to organofunctional groups in the RTV silicone composition. In one embodiment, the ratio of Si—H groups to organofunctional groups is from about 0.2:1 to about 20:1. In another embodiment, the ratio is from about 1:1 to about 10:1. In yet another embodiment, the ratio is from about 1.5:1 to about 4:1.

Alternatively, the amount of the crosslinking agent in the RTV silicone composition can be adequately described in terms of parts by weight of the crosslinkable polysiloxane. In one embodiment, the RTV silicone composition contains from about 0.01 to about 50 parts by weight of the crosslinking agent per 100 parts by weight of the crosslinkable polysiloxane. In another embodiment, the RTV silicone composition contains from about 0.1 to about 25 parts by weight of the crosslinking agent per 100 parts by weight of the crosslinkable polysiloxane. In yet another embodiment, the RTV silicone composition contains from about 1 to about 10 parts by weight of the crosslinking agent per 100 parts by weight of the crosslinkable polysiloxane.

The RTV silicone composition contains a catalyst, which is typically a metal catalyst, typically a transition metal catalyst, and even more typically a platinum catalyst. The crosslinkable polysiloxane and the crosslinking agent react in the presence of the catalyst. Other catalysts include peroxide catalysts, oxime catalysts, acetoxy catalysts, hydroxyl catalysts, aziridine catalysts, iron catalysts, tin catalysts, titanium catalysts, palladium catalysts, and the like.

In one embodiment, the RTV silicone composition contains from about 1 to about 500 parts per million (ppm) of a metal catalyst such as platinum. In another embodiment, the RTV silicone composition contains from about 10 to about 250 ppm of a metal catalyst such as platinum. In yet another embodiment, the RTV silicone composition contains from about 25 to about 200 ppm of a metal catalyst such as platinum. The catalyst can be a solid metal catalyst deposited on gamma-alumina or charcoal or it can be a solubilized metal complex such as platinum complex. The solubilized metal complexes are preferred since they tend to be more reactive. Solubilized platinum complexes include those having the formula, $(PtCl_2 \cdot \text{Olefin})_2$ and $H(PtCl_3 \cdot \text{Olefin})$ as described in U.S. Pat. No. 3,159,601, which is hereby incorporated by reference in this regard. The olefin shown in the previous two chemical formulae can be almost any type of olefin, but is preferably an alkenylene having from about 2 to about 8 carbon atoms, a cyclo alkenylene having from about 5 to about 7 carbon atoms or styrene. Specific olefins utilized in the above formulae are ethylene, propylene, the various isomers of butylene octylene, cyclopentene, cyclohexene, cycloheptene, etc. For example, such platinum catalysts include [(CH2CH2).PtCl2]2; (PtCl2.C3H6)2, etc. A further platinum containing material suitable for use in the RTV silicone composition is a platinum chloride cyclopropane complex $(PtCl_2 \cdot C_3H_6)_2$ described in U.S. Pat. No. 3,159,662, which is hereby incorporated by reference in this regard. For example, such platinum catalysts include the reaction product of chloroplatinic acid hexahydrate and octyl alcohol, etc.

In another embodiment, the platinum containing material can be a complex formed from chloroplatinic acid with up to about two moles per gram of platinum of at least one of an alcohol, ether, aldehyde as described in U.S. Pat. No. 3,220,972, which is hereby incorporated by reference in this regard. In another embodiment, the catalyst is that disclosed U.S. Pat. No. 3,419,513, which is hereby incorporated by reference in this regard.

In yet another embodiment, the platinum catalyst employed is disclosed in U.S. Pat. No. 3,775,452, which is hereby incorporated by reference in this regard. Generally speaking, this type of platinum complex is formed by reacting chloroplatinic acid containing about 4 moles of water of hydration with tetravinylcyclotetrasiloxanes in the presence of sodium bicarbonate in an ethanol solution. The Karstedt platinum catalyst is typically a solubilized platinum complex of platinum with a linear or cyclic low molecular weight vinyl terminated polysiloxane polymer. In still yet another embodiment, the catalyst employed is disclosed in U.S. Pat. No. 3,516,946, which is hereby incorporated by reference in this regard, which comprises a complex formed between platinum and a vinyl-containing cyclopolysiloxane such as methyl, vinyl cyclotetrasiloxane.

In one embodiment, the catalyst is a solubilized platinum complex produced by complexing platinum with tetravinyldimethyldisiloxane which is a Karstedt catalyst. The reaction is carried out by mixing the silanol containing polymer with the hydride and the solubilized platinum complex as disclosed above.

In another embodiment, the Karstedt platinum catalysts are described in at least one of U.S. Pat. Nos. 3,715,334; 3,775,452 and 3,814,730 which are hereby incorporated by reference in this regard. To produce a Karstedt catalyst according to this embodiment, utilized are a platinum halide and a complexing material in the form of an unsaturated organosilicon material containing at least one of the three:

(1) unsaturated silanes having empirical Formula VII:

  Formula VII wherein each R is independently free of aliphatic unsaturation and is a monovalent hydrocarbon radicals, each R' is independently a monovalent aliphatically unsaturated hydrocarbon radical, each X is independently a hydrolyzable radical, c is from 1 to about 10,000, b is greater than about 2 and the sum of a, b and z equals the sum of 2 and two times c for a linear or branched silane and wherein c is from about 4 to about 18 and the sum of a, b and z equals two times c for a cyclic silane;

(2) unsaturated linear or branched siloxanes of Formula VIII:

  Formula VIII wherein R and R' are as defined above, f is from about 2 to about 10,000, e is greater than about 2 and the sum of d and e equals the sum of 2 and two times f; and (3) unsaturated cyclic siloxanes of Formula IX

  Formula IX wherein R and R' are as defined above, f is from about 3 to about 18, and the sum of d and e equals two times f.

In this embodiment, the Karstedt catalyst is made by effecting contact between an unsaturated organosilicon material as defined by at least one of Formulae VII, VIII and IX above, and a platinum compound, such as a platinum halide, to provide for the production of a mixture sometimes having a concentration of inorganic halogen; if present, treating the resulting mixture to effect the removal of inorganic halogen; and recovering therefrom a platinum-siloxane complex. In a preferred embodiment, the recovered platinum-siloxane complex has less than about 0.1 gram atoms of halogen, per gram atom of platinum, and more preferably is substantially halogen free.

In this embodiment, examples of R radicals include alkyl radicals such as methyl, ethyl, propyl, butyl, hexyl, heptyl, octyl, etc.; cycloalkyl radicals such as cyclohexyl, cycloheptyl, etc.; aryl radicals such as phenyl, methyl, tolyl, xylyl, etc.; aralkyl radicals such as benzyl, phenylethyl, phenylpropyl, etc. Also in this embodiment, examples of R' radicals include aliphatically unsaturated radicals such as ethynyl, 1-propynl, etc.; vinyl, allyl, and cycloalkenyl radicals, such as cyclopentenyl, cyclohexenyl, cycloheptenyl, cyclooctenyl, etc.

It is desirable that neither the R nor the R' radicals have chemically combined halogen since the presence of such halogen attached to the hydrocarbon group in the platinum complex in some instances acts to inhibit the catalysis effected by the complex. Accordingly, it is preferred to catalyze silanes and siloxanes of Formulae VII, VIII and IX in forming the platinum catalyst of the present invention that do not have combined halogen.

Examples of unsaturated silanes described by Formula VII include tetravinylsilane, tri-allylmethylsilane, divinyidimethylsilane, tri-vinylphenylsilane, divinylmethylphenylsilane, divinylmethylethoxysilane, divinylmethylacetoxysilane, etc. Examples of unsaturated siloxanes described by Formula VIII include disiloxanes of Formula X:

  Formula X wherein R, R', are as defined above, h has a value per silicon atom of at least one and the sum of g and h, per silicon atom, is equal to about 3. Examples of disiloxanes described by Formula X include symdivinyltetramethyldisiloxane, 1,3-divinyltetramethyldisiloxane, hexavinyldisiloxane, 1,1,3-trivinyltriethyldisiloxane, symtetravinyldimethyldisiloxane, etc. Examples of unsaturated siloxanes described by Formula IX include cyclopolysiloxanes such as 1,3,5-trivinyl-1,3,5-trimethylcyclotrisiloxane, and 1,3,5,7-tetraallyl-1,3,5,7-tetraphenylcyclotetrasiloxane 1,3-divinyloctamethylcyclopentasiloxane, etc.

In another embodiment, the platinum-siloxane complexes of platinum and organosiloxanes of Formulae VIII and IX are made utilizing a platinum halide, and an unsaturated linear, branched or cyclic siloxane of Formula VIII or IX having at least one structural unit of Formula XI

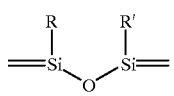

Formula XI wherein the unsatisfied valences of the above structural unit can be satisfied by R, R' and oxygen radicals and where R and R' are as previously defined.

The platinum compounds which can be employed in making the catalysts include $H_2PtCl_6 \cdot nH_2O$ and metal salts such as $NaHPtCl_6 \cdot nH_2O$, $KHPtCl_6 \cdot nH_2O$, $Na_2PtCl_6 \cdot nH_2O$, $K_2PtCl_6 \cdot nH_2O$, $PtCl_4 \cdot nH_2O$ and platinous type halides such as $PtCl_2$, $Na_2PtCl_4 \cdot nH_2O$, $H_2PtCl_4 \cdot nH_2O$, $NaHPtCl_4 \cdot nH_2O$, $KHPtCl_4 \cdot nH_2O$, and $K_2PtBr_4$.

The amount of the platinum complex component is sufficient to provide the desired degree of crosslinking of the RTV silicone composition within a reasonable time, such as within about 2 hours. In a preferred embodiment, the desired degree of crosslinking of the RTV silicone composition within about 1 hour. In part, due to the wide range of acceptable molecular weights for the crosslinkable polysiloxane, the amount can in one sense be suitably described in terms of the ratio of Pt atoms to organofunctional groups in the RTV silicone composition. In one embodiment, the ratio of Pt atoms to organofunctional groups is from about 1:2 to about 1:500. In another embodiment, the ratio of Pt atoms to organofunctional groups is from about 1:10 to about 1:200. In yet another embodiment, the ratio of Pt atoms to organofunctional groups is from about 1:30 to about 1:70.

The RTV silicone composition may optionally contain one or more additives. Additives include fillers, medicaments, stabilizers, thickeners, pigments, dyes and antioxidants. In one embodiment, the RTV silicone composition contains from about 0.001 % to about 35% by weight of at least one additive. In another embodiment, the RTV silicone composition contains from about 0.01 % to about 30% by weight of at least one additive. In another embodiment, the RTV silicone composition contains from about 0.1% to about 25% by weight of at least one additive.

Examples of fillers include fumed silica, quartz powder, glass fibers, carbon, metal oxides such as iron oxide, titanium oxide, and cerium oxide, and metal carbonates such as calcium carbonate and magnesium carbonate. Fumed silica is preferred since it can maintain cured RTV silicone compositions transparent. Fumed silicas are available from Degussa under the trade designation Aerosil®.

Stabilizers specifically include amine stabilizers. Suitable thickeners are the swelling agents customarily used for gel formation in galenic pharmacy. Examples of suitable thickeners include natural organic thickeners, such as agar—agar, gelatin, gum arabic, a pectin, etc., modified organic natural compounds, such as carboxymethylcellulose or cellulose ethers, or fully synthetic organic thickeners, such as polyacrylic compounds, vinyl polymers, or polyethers.

Medicaments include analgesic-antirheumatic agents and antibiotics. Analgesic-antirheumatic agents include phenylbutazone, oxyphenbutazone, indomethacin, naproxen, ibuprofen, acetaminophin, acetylsalicylic acid, etc. Antibiotics include various penicillins, tetracyclines, streptomycins, etc.

Examples of RTV silicone compositions that are commercially available include silicon RTVs from Nusil Technology, including those under the trade/product designations CF15-2186, CF19-2186, MED1-4013, and MED2-4013; and RTV silicone solutions from Factor II, Inc./Dow Corning, including those under the trade/product designations MDX4-4159, A-2186, and A-588. Preferred RTV silicone compositions are the MED1-4013 and CF19-2186 available from Nusil Technology. Various other RTV silicone compositions, crosslinkable polysiloxanes, crosslinking agents, catalysts and additives are available from Silicones, Inc., Precision Silicones, Inc., the Walco Materials Group of Synair Corp., General Electric, Bayer, Hulls America, Shiastu, Shin Etsu, Rhone Poulenc, Wacker Silicones, Degussa, Dow Corning, and Cabot Corp.

Just prior to applying the RTV silicone composition to a wound, all of the components are mixed. In a preferred embodiment, the RTV silicone composition is made from a two part RTV silicone composition wherein one part contains the crosslinking agent and the crosslinkable polysiloxane while a second part contains the catalyst and the crosslinkable polysiloxane. One or both parts optionally contain additives. Once all of the components are mixed, the composition begins to cure (crosslinking is commenced).

In a preferred embodiment, a first part has a viscosity from about 60,000 to about 120,000 cps while the second part has a viscosity from about 40,000 to about 100,000 cps. In another preferred embodiment, a first part has a viscosity from about 70,000 to about 100,000 cps while the second part has a viscosity from about 50,000 to about 90,000 cps.

The work time of the mixed RTV silicone composition is from about 2 minutes to about 15 minutes. In a preferred embodiment, the work time of the mixed RTV silicone composition is from about 3 minutes to about 12 minutes. The work time is the amount of time the mixed RTV silicone composition is a substantially flowable state. As such, the RTV silicone composition is easily applied to a wound. After application, the RTV silicone composition is smoothed to a desired thickness. The mixed RTV silicone composition is substantially tack-free about 30 minutes after mixing. In a preferred embodiment, the mixed RTV silicone composition is substantially tack-free about 30 minutes after mixing. After about 45 minutes after all of the components are mixed, it is difficult to apply the RTV silicone composition to a wound.

In a preferred embodiment, a release agent is applied to objects used to apply the RTV silicone composition to a wound. For example, if applied by hand, a release agent is applied to the rubber gloves cover an applicators hands to minimize the amount of RTV silicone composition that may adhere to the gloves.

It is difficult to identify a precise time when curing is completed. When the composition has substantially cured, a flexible membrane is formed. Typically, the RTV silicone composition is substantially cured at least about 3 hours after application to a wound. In another embodiment, the RTV silicone composition is substantially cured at least about 6 hours after application to a wound. In yet another embodiment, the RTV silicone composition is substantially cured at least about 12 hours after application to a wound. The RTV silicone composition may take 1 or 2 days to fully cure, but substantial curing is adequate for the purposes of this invention.

In a preferred embodiment, no padding is applied to the wound in addition to the RTV silicone composition. In this connection, it is not necessary to apply a textile or plastic support strip with the RTV silicone composition.

The thickness of the RTV silicone composition is sufficient to act as barrier to infection causing species as well as sufficient to retain moisture in the wound. In one embodiment, the thickness of the RTV silicone composition applied to the wound is from about 0.1 mm to about 5 mm.

In another embodiment, the thickness of the RTV silicone composition applied to the wound is from about 0.25 mm to about 3 mm. In another embodiment, the thickness of the RTV silicone composition applied to the wound is from about 0.5 mm to about 2 mm.

The RTV silicone composition may be custom fit to any contoured or shaped surface. This is an advantage over and in contrast with prefabricated bandaids or dressings, or dressings that must be cut and fit to a wound.

In one embodiment, the RTV silicone composition is transparent or substantially transparent. The development of a transparent membrane permits visual observation and monitoring of the wound as it heals. The transparent membrane also provides a relatively inconspicuous dressing for the wound.

The RTV silicone composition forms a membrane that is continuous or substantially continuous. The continuous nature of the membrane contributes to the ability of the membrane to retain moisture in the wound. The continuous nature of the membrane contributes to the ability of the membrane to act as a bacterial barrier. In one embodiment, the RTV silicone membrane is free or at least substantially free of air bubbles.

Any wound may be treated in accordance with the present invention. Such wounds include cuts, abrasions traditional surgical wounds (such as those resulting from the use of a scalpel) and laser surgery wounds. In a preferred embodiment of the present invention, the wound treated is a laser surgery wound. Laser surgery wounds are caused by any suitable medical laser including carbon dioxide lasers, YAG lasers, erbium YAG lasers, ruby lasers, Alexandrite lasers, Q-switched Alexandrite lasers, Q-switched neodymium YAG lasers, frequency doubled neodymium YAG lasers, copper vapor lasers, argon lasers, and pulsed dye lasers.

The RTV silicone composition membrane remains on the wound for a time sufficient to permit healing of the wound. In one embodiment, the RTV silicone composition forming a membrane remains on the wound at least about 1 day. In another embodiment, the RTV silicone composition forming a membrane remains on the wound at least about 2 days. In yet another embodiment, the RTV silicone composition forming a membrane remains on the wound at least about 4 days. In still yet another embodiment, the RTV silicone composition forming a membrane remains on the wound at least about 6 days. In a preferred embodiment, the RTV silicone composition forming a membrane remains on the wound from about 7 days to about 10 days. Although not typically necessary, on wounds in extremely mobile areas of the body, it may be required to change the silicone composition dressing every 1, 2 or 3 days.

After the RTV silicone composition has been on a wound for at least about 1 day, and healing is promoted and/or substantially completed, the RTV silicone membrane is removed by gently peeling it from the wound. The healed wound is characterized by decreased redness, moistness, minimal scarring. The healed wound is generally in better condition than similar wounds covered with conventional dressings. Especially with wounds caused by laser surgery, the healed laser surgery wound is generally in better condition than similar wounds covered with conventional dressings.

While the invention has been explained in relation to its preferred embodiments, it is to be understood that various modifications thereof will become apparent to those skilled in the art upon reading the specification. Therefore, it is to be understood that the invention disclosed herein is intended to cover such modifications as fall within the scope of the appended claims.

What is claimed is:

1. A method of treating a wound, comprising:
    applying to the wound a room temperature vulcanizing silicone composition comprising a crosslinkable polysiloxane, a crosslinking agent, and a catalyst;
    permitting the room temperature vulcanizing silicone composition to cure thereby forming a membrane having a thickness from about 0.1 mm to about 5 mm; and
    removing the membrane from the wound after at least about 1 day,
    wherein the room temperature vulcanizing silicone composition comprises: (A) from about 0.001% to about 35% by weight of at least one additive selected from fillers, medicaments, stabilizers, thickeners, pigments, dyes and antioxidants; and (B) from about 1 to about 200 ppm of the catalyst.

2. The method of claim 1, wherein the room temperature vulcanizing silicone composition is a platinum catalyzed silicone elastomer.

3. The method of claim 1, wherein the crosslinkable polysiloxane comprises a polysiloxane having one or more functional groups, the functional groups comprising at least one of vinyl, allyl, 1-hexenyl and cyclohexenyl groups.

4. The method of claim 1, wherein the crosslinking agent comprises an organohydrogenpolysiloxane containing at least one silicon-hydrogen linkage.

5. The method of claim 1, wherein the catalyst comprises a solubilized platinum complex.

6. The method of claim 1, wherein the room temperature vulcanizing silicone composition comprises from about 0.1% to about 25% by weight fumed silica.

7. The method of claim 1, wherein the membrane has a thickness from about 0.5 mm to about 2 mm.

8. A method of treating a laser surgery wound, comprising:
    combining a first composition comprising a first crosslinkable polysiloxane and a crosslinking agent with a second composition comprising a second crosslinkable polysiloxane and a platinum catalyst to form a room temperature vulcanizing silicone composition comprising the first and second crosslinkable polysiloxanes, the crosslinking agent, and the platinum catalyst;
    applying to the laser surgery wound the room temperature vulcanizing silicone composition;
    permitting the room temperature vulcanizing silicone composition to cure thereby forming a substantially transparent membrane having a thickness from about 0.25 mm to about 3 mm; and
    removing the substantially transparent membrane from the laser surgery wound after at least about 2 days,
    wherein at least one of the first composition and/or the second composition, and the room temperature vulcanizing silicone composition comprises: (A) from about 0.001% to about 35% by weight of at least one additive selected from fillers, medicaments, stabilizers, thickeners, pigments, dyes and antioxidants; and (B) from about 1 to about 200 ppm of the platinum catalyst.

9. The method of claim 8, wherein the room temperature vulcanizing silicone composition comprises from about 10% to about 99% by weight of the first and second crosslinkable polysiloxanes; from about 0.01 to about 50 parts by weight of the crosslinking agent per 100 parts by weight of the first and second crosslinkable polysiloxanes.

10. The method of claim 8, wherein the first and second crosslinkable polysiloxanes comprise the same crosslinkable polysiloxane.

11. The method of claim 8, wherein at least one of the first crosslinkable polysiloxane and the second crosslinkable polysiloxane comprise a compound represented by Formula II:

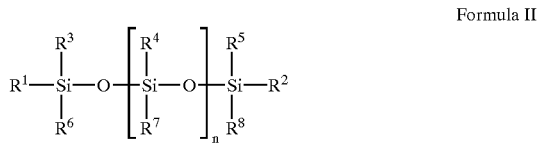

Formula II wherein $R^1$ and $R^2$ are independently hydrogen, hydroxyl, and organofunctional groups, $R^3$, $R^4$, $R^5$, $R^6$, $R^7$, and $R^8$ are independently hydrogen, and hydrocarbyl groups containing from 1 to about 20 carbon atoms and n is from about 10 to about 6,000.

12. The method of claim 8, wherein the crosslinking agent comprises an organohydrogenpolysiloxane containing at least about two silicon-hydrogen linkage.

13. The method of claim 8, wherein at least one of the first composition and second composition, and the room temperature vulcanizing silicone composition comprises from about 0.01% to about 30% by weight of at least one additive selected from fillers, medicaments, stabilizers, thickeners, pigments, dyes and antioxidants.

14. The method of claim 8, wherein the substantially transparent membrane is removed from the laser surgery wound after at least about 4 days.

15. A method of treating a laser surgery wound, comprising:
combining a first composition comprising a first crosslinkable polysiloxane and a crosslinking agent with a second composition comprising a second crosslinkable polysiloxane and a platinum catalyst to form a room temperature vulcanizing silicone composition comprising the first and second crosslinkable polysiloxanes, the crosslinking agent, and the platinum catalyst;
applying to the laser surgery wound the room temperature vulcanizing silicone composition;
permitting the room temperature vulcanizing silicone composition to cure thereby forming a substantially transparent membrane having a thickness from about 0.25 mm to about 3 mm; and
removing the substantially transparent membrane from the laser surgery wound after at least about 4 days,
wherein at least one of the first composition and/or the second composition, and the room temperature vulcanizing silicone composition comprises: (A) from about 0.001% to about 35% by weight of at least one additive selected from fillers, medicaments, stabilizers, thickeners, pigments, dyes and antioxidants; and (B) from about 1 to about 200 ppm of the platinum catalyst.

16. The method of claim 15, wherein the laser surgery wound is caused by one of carbon dioxide lasers, YAG lasers, erbium YAG lasers, ruby lasers, Alexandrite lasers, Q-switched Alexandrite lasers, Q-switched neodymium YAG lasers, frequency doubled neodymium YAG lasers, copper vapor lasers, argon lasers, and pulsed dye lasers.

17. The method of claim 15, wherein the room temperature vulcanizing silicone composition is applied to the laser surgery wound within about 45 minutes of combining the first composition with the second composition.

18. The method of claim 15, wherein the room temperature vulcanizing silicone composition comprises from about 20% to about 90% by weight of the first and second crosslinkable polysiloxanes; and from about 0.1 to about 25 parts by weight of the crosslinking agent per 100 parts by weight of the first and second crosslinkable polysiloxanes.

19. The method of claim 15, wherein at least one of the first composition and second composition, and the room temperature vulcanizing silicone composition comprises from about 0.01% to about 30% by weight of at least one additive selected from fillers, medicaments, stabilizers, thickeners, pigments, dyes and antioxidants.

20. The method of claim 15, wherein at least one of the first composition and second composition, and the room temperature vulcanizing silicone composition comprises from about 0.1% to about 25% by weight of fumed silica.

21. A method of treating a wound, comprising:
applying to the wound a room temperature vulcanizing silicone composition comprising a crosslinkable polysiloxane, a crosslinking agent, and a catalyst;
permitting the room temperature vulcanizing silicone composition to cure thereby forming a membrane having a thickness from about 0.1 mm to about 5 mm; and
removing the membrane from the wound after at least about 1 day,
wherein the room temperature vulcanizing silicone composition comprises from about 1 to about 200 ppm of the catalyst.

22. The method of claim 21, wherein the room temperature vulcanizing silicone composition is a platinum catalyzed silicone elastomer.

23. The method of claim 21, wherein the crosslinkable polysiloxane comprises a polysiloxane having one or more functional groups, the functional groups comprising at least one of vinyl, allyl, 1-hexenyl and cyclohexenyl groups.

24. The method of claim 21, wherein the crosslinking agent comprises an organohydrogenpolysiloxane containing at least one silicon-hydrogen linkage.

25. The method of claim 21, wherein the catalyst comprises a solubilized platinum complex.

26. The method of claim 21, wherein the room temperature vulcanizing silicone composition further comprises fumed silica.

27. A method of treating a laser surgery wound, comprising:
combining a first composition comprising a first crosslinkable polysiloxane and a crosslinking agent with a second composition comprising a second crosslinkable polysiloxane and a platinum catalyst to form a room temperature vulcanizing silicone composition comprising the first and second crosslinkable polysiloxanes, the crosslinking agent, and the platinum catalyst;
applying to the laser surgery wound the room temperature vulcanizing silicone composition;
permitting the room temperature vulcanizing silicone composition to cure thereby forming a substantially transparent membrane having a thickness from about 0.25 to about 3 mm; and
removing the substantially transparent membrane from the laser surgery wound after at least about 2 days,
wherein at least one of the first composition and/or the second composition, and the room temperature vulcanizing silicone composition comprises from about 1 to about 200 ppm of the platinum catalyst.

28. The method of claim 27, wherein the room temperature vulcanizing silicone composition comprises from about 10% to about 99% by weight of the first and second crosslinkable polysiloxanes; and from about 0.01 to about 50 parts by weight of the crosslinking agent per 100 parts by weight of the first and second crosslinkable polysiloxanes.

29. The method of claim 27, wherein the first and second crosslinkable polysiloxanes comprise the same crosslinkable polysiloxane.

30. The method of claim 27, wherein the crosslinking agent comprises an organohydrogenpolysiloxane containing at least about two silicon-hydrogen linkage.

31. The method of claim 27, wherein at least one of the first composition and second composition, and the room temperature vulcanizing silicone composition further comprises at least one of fillers, medicaments, stabilizers, thickeners, pigments, dyes and antioxidants.

32. A method of treating a laser surgery wound, comprising:

combining a first composition comprising a first crosslinkable polysiloxane and a crosslinking agent with a second composition comprising a second crosslinkable polysiloxane and a platinum catalyst to form a room temperature vulcanizing silicone composition comprising the first and second crosslinkable polysiloxanes, the crosslinking agent, and the platinum catalyst;

applying to the laser surgery wound the room temperature vulcanizing silicone composition;

permitting the room temperature vulcanizing silicone composition to cure thereby forming a substantially transparent membrane having a thickness from about 0.25 mm to about 3 mm; and removing the substantially transparent membrane from the laser surgery wound after at least 4 days, wherein at least one of the first composition and/or the second composition, and the room temperature vulcanizing silicone composition comprises from about 1 to about 200 ppm of the platinum catalyst.

33. The method of claim 32, wherein the laser surgery wound is caused by one of carbon dioxide lasers, YAG lasers, ebrium YAG lasers, ruby lasers, Alexandrite lasers, Q-switched Alexandrite lasers, Q-switched neodymium YAG lasers, frequency doubled neodymium YAG lasers, copper vapor lasers, argon lasers, and pulsed dye lasers.

34. The method of claim 32, wherein the room temperature vulcanizing silicone composition is applied to the laser surgery wound within about 45 minutes of combining the first composition with the second composition.

35. The method of claim 32, wherein the room temperature vulcanizing silicone composition comprises from about 20% to about 90% by weight of the first and second crosslinkable polysiloxanes; and from about 0.1 to about 25 parts by weight of the crosslinking agent per 100 parts by weight of the first and second crosslinkable polysiloxanes.

36. The method of claim 32, wherein at least one of the first composition and second composition, and the room temperature vulcanizing silicone composition further comprises at least one of fillers, medicaments, stabilizers, thickeners, pigments, dyes and antioxidants.

37. The method of claim 32, wherein at least one of the first composition and second composition, and the room temperature vulcanizing silicons composition further comprises fumed silica.

* * * * *